Figure 1:
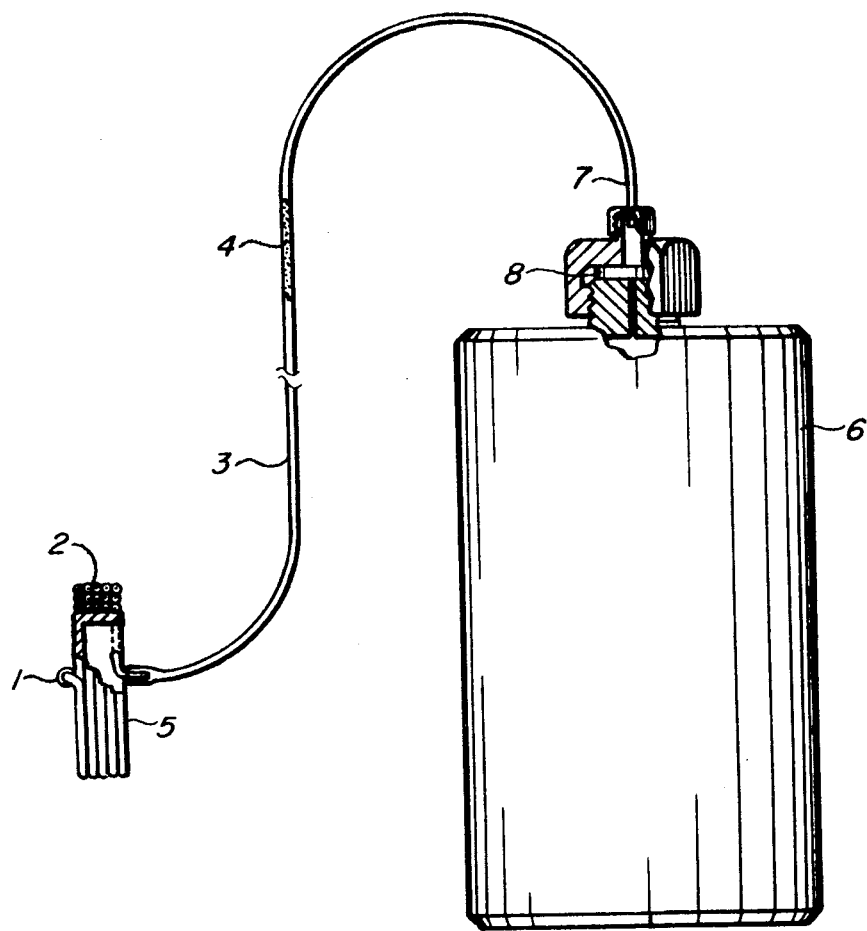
Figure 2:
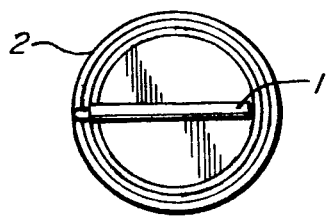

United States Patent [19]

Clark et al.

[11] 4,455,881
[45] Jun. 26, 1984

[54] AEROSOL EXPOSURE MONITORING DEVICE

[75] Inventors: Reginald H. Clark, Kingston; Joel R. Nodelman, Edmonton, both of Canada

[73] Assignee: Queen's University at Kingston, Kingston, Canada

[21] Appl. No.: 390,755

[22] Filed: Jun. 21, 1982

[30] Foreign Application Priority Data

Jul. 7, 1981 [CA] Canada ................................. 381255

[51] Int. Cl.³ .............................................. G01N 1/24
[52] U.S. Cl. ............................ 73/863.21; 73/863.23; 73/864.52
[58] Field of Search ........... 73/863.21, 864.91, 864.52, 73/863.22, 864, 864.11, 863.23; 128/730; 604/159

[56] References Cited

U.S. PATENT DOCUMENTS

| | | | |
|---|---|---|---|
| 3,327,898 | 6/1967 | Farr | 73/864.11 X |
| 3,518,815 | 7/1970 | McFarland et al. | 73/863.22 |
| 3,618,393 | 11/1971 | Principe et al. | 73/864.52 |
| 3,681,030 | 8/1972 | Natelson | 73/864.11 |
| 4,040,299 | 8/1977 | Snyder | 73/864.52 |

*Primary Examiner*—Daniel M. Yasich
*Attorney, Agent, or Firm*—Richard J. Hicks; Stanley E. Johnson

[57] ABSTRACT

A light weight and inexpensive sampling device to sample the respirable fraction of aerosols in a work environment on a continuous basis is described. The device consists of a short length of capillary tubing having an internal diameter of about 1.3 mm in a series with a somewhat longer length of capillary tubing having an internal diameter of about 0.5 mm which acts as a collector or sampler and which is in turn connected to an aspirating device. The sampler tube may be wound on a spool which is so small that the entire device is button sized and may be conveniently worn on the lapel as a personal monitoring device. The trapped respirable aerosol particles may be washed out of the sampler periodically for counting and/or chemical analysis.

9 Claims, 6 Drawing Figures

AEROSOL EXPOSURE MONITORING DEVICE

This invention relates to a device for sampling the respirable fraction of aerosols contained in the atmosphere, and in particular work environments, on a continuous basis.

Many aerosol sampling devices have, of course, been proposed heretofore which generally employ a filter element consisting of a porous filter disc in a housing which is connected by tubing to an electro-mechanical aspirating device. As aspiration proceeds the flow of gas through the filter decreases as the porous element becomes less porous due to the build-up of collected aerosol therein and precautions must be taken to adjust the aspirating device to accurately estimate the volume of air which is actually sampled. Such devices are relatively large, cumbersome and expensive and for these reasons are confined in their use to test and research functions and are not generally available to monitor the individual intake, on a routine base, of aerosols by, for example, workers in a dusty or otherwise hazardous work environment. Furthermore, as the filtered aerosol must, for analysis purposes, be either extracted from the filter element or examined microscopically, the cost of analysis limits the routine use of these units for personal monitoring. It will also be appreciated that the filter element will remove not only the respirable portion of the aerosol, i.e. that fraction of the aerosol likely to be retained in the human lungs, but also the non-respirable portion and the separation of these two portions, as it is generally only the respirable portion which is of concern or interest, is complicated and requires relatively sophisticated and expensive equipment.

There is, therefore, a need for a simple, inexpensive aerosol collection device which can be used on a routine basis for personal monitoring of the respirable portion of an aerosol, from which the collected sample can be quickly and easily removed for analysis and which does not require expensive compensation devices to allow for changes in resistance to gas flow therethrough. If made small enough there is also a need to measure air quality within a mask or hooded helmet.

It is an object of the present invention to provide a sampler which fulfils the aforesaid need.

Thus, by one aspect of this invention there is provided a device for sampling respirable aerosols contained in an atmosphere, comprising:

a selector capillary tube open at one end thereof to said atmosphere;

a sampling capillary tube in fluid communication with the other end of said selector tube; and aspiration means, connected in series fluid communication with said sampling tube, so as to draw said atmosphere through said selector and sampling tubes at a selected aspiration rate;

said selector tube having a selected length and selected internal diameter so as to precipitate therein non-respirable aerosols in said atmosphere at said aspiration rate; and said sampling tube having a relatively longer selected length and relatively smaller selected internal diameter so as to selectively precipitate therein substantially all respirable aerosols in said atmosphere at said selected aspiration rate.

The invention will be described in more detail hereinafter with reference to the drawings in which:

FIG. 1 is an isometric view of a sampler of the present invention;

FIG. 2 is a plan view of the sampler spool of FIG. 1;

FIG. 3 is a graph illustrating the relation between predicted distribution of particle size and standard definitions; and FIGS. 4*a*, *b* and *c* are graphs comparing the experimental and theoretical particle penetration through selectors of various lengths.

The device of the present invention, as illustrated in FIG. 1 comprises a relatively short length (of the order of 0.5–4 cm and preferably 2 cm) of selector capillary 1 of selected internal diameter of the order of 0.75 to 2.0 mm, preferably 1.3 mm, the outlet end of which coupled in series with the inlet end of a relatively much longer length (of the order of 20–100 cm, preferably 40 cm) of sampling capillary 2 having a selected smaller internal diameter than capillary 1, of the order of 0.25 to 1.0 mm. Generally, but not essentially, the capillary is a relatively flexible and inexpensive thermoplastics material tubing, although glass capillary or the like may equally well be used. The outlet of capillary 2 is coupled in series with an aspirator tube 3 so as to provide a fluid flowpath through the device to an aspirator device such as a vacuum tank 6 provided with a syringe needle connector 7 and flow restriction orifice plate 8. Any well known type of aspirator device may be employed, such as a vibratory or peristaltic pump, a bottled gas jet ejector or the small evacuated vessel shown in FIG. 1. If it is desired to sample noxious or other gases during aspiration, this may be readily effected by including a section of tubing 4 containing an appropriate absorbent in the flowpath between the sampler capillary 2 and the aspirator. For convenience, the sampler capillary tubing 2 may be wound on a small spool or reel 5. A spool having a diameter of about 2 cm to 5 cm and about 0.25–2 cm thick has been found adequate for this purpose when using flexible thermoplastics material, so that the entire sampling unit is rosette or button sized, and can easily be worn on the lapel or in the manner of a radiation film badge.

In operation, the selector capillary 1 serves to remove the larger aerosols or non-respirable aerosol fraction and the sampler capillary removes the smaller and respirable aerosols, in a manner closely akin to the action of the lungs. Because the larger aerosols are trapped in the selector capillary 1, there is a reduced probability of blockage of the sampling capillary 2. The selector capillary 1 also serves to fractionate the dust particles, according to their size, so that the sampler capillary 2 collects particles in the respirable range in approximate proportions defined by standard definitions for respirable sizes. The quantity of solid particles collected in the sampler capillary 2 may be readily determined by disconnecting the collector section and washing out the particles directly or indirectly into a particle counting machine or an automatic commercially available chemical analysis machine. If desired, the capillary sampler may be coated internally to insure adherence of particles, by deposit, for example, of an oil film or other soluble material.

It is emphasized that the sampler device fitted with a selector tube does not measure the total aerosol concentration, but only that fraction which is likely to be retained in the lungs. For this reason the concentrations measured by the present sampler are lower than those measured by the "total captive" devices currently in use. For example, in comparison to a standard millipore filter sampler, the sampler of the present invention may only collect about 20% of the total concentration recorded by the millipore filter.

It will be appreciated that the aspiration velocity and dimensions, both diameter and length, of the selector and sampler sections may be varied, to suit the specific dust to be sampled and thus provide for the fractionation of the respirable dust fraction. The length of the sampling section required to capture the respirable fraction is dependent upon both the internal diameter of the tubing and the aspiration velocity. The approximate length may be estimated from relationships developed by Heyder (ref: J. Aerosol Science 1975, 6 133–137) and Thomas (ref: Air Pollution Control Assoc. J., 1958, 8 32–34 and Proc. Royal Irish Acad. 1935, 43a, 1–4). A length of between 30 and 50 cms, preferably 40 cms of 0.5 mm I.D. tubing is adequate for the efficient capture of most industrial solid dust particles at aspiration velocities varying from about 3 cm/sec up to about 35 cm/sec.

Figure 3:
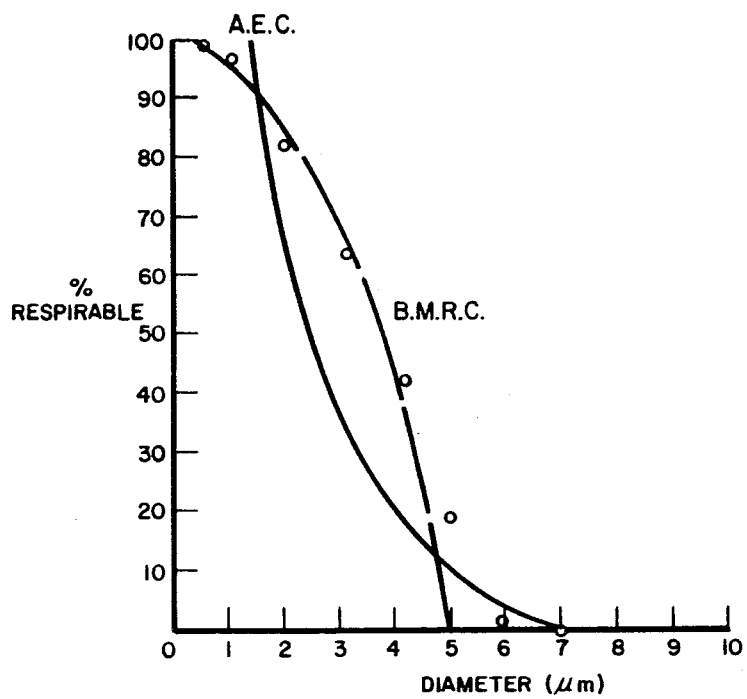
Figure 4A:
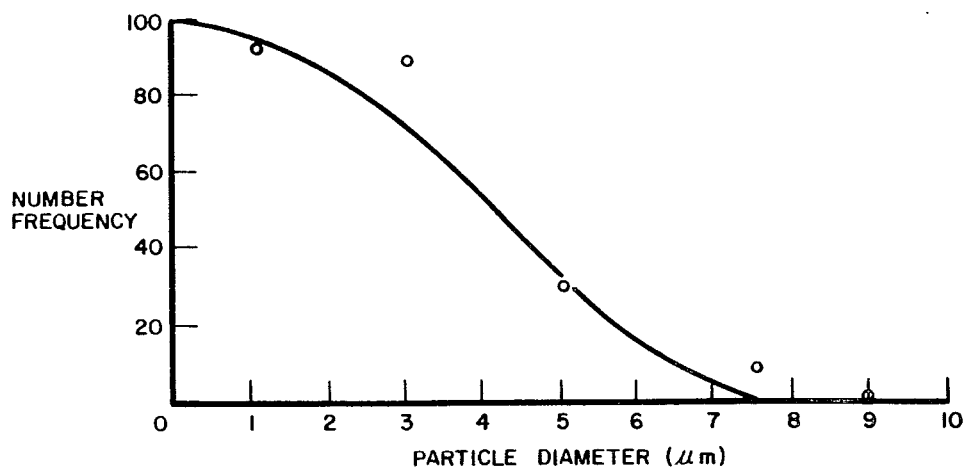
Figure 4B:
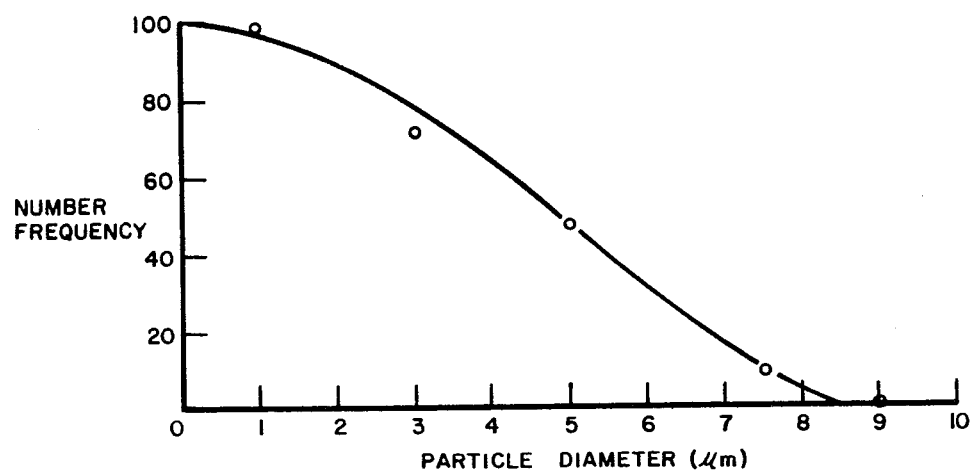
Figure 4C:
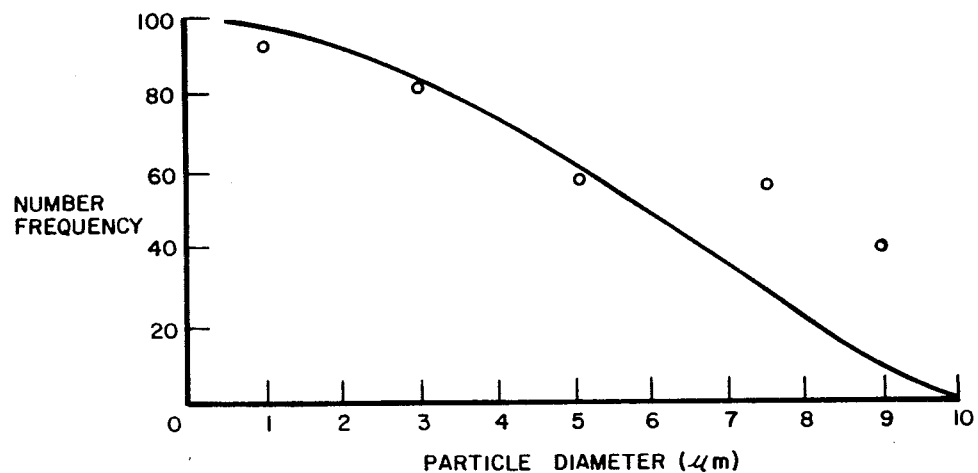

It is also possible to estimate the degree of fractionation and the particle size distribution of the solid collected in the sampling tube. FIG. 3 illstrates the comparison between the predicted distribution of particle size and the Atomic Energy Commission and British Medical Research Council definitions of respirable particle size distributions for the typical sampler dimensions previously given. As may be seen from FIGS. 4a, 4b or 4c, which employ selector lengths of 25 mm, 20 mm and 15 mm respectively at an aspiration velocity of 20 cm/sec, the experimental agreement with the theoretical estimates is good if an allowance is made for entrance effects observed with short selector lengths. Thus by suitable adjustment of the aspiration velocity or the sampler dimensions the respirable concentration of any aerosol can be determined.

By way of illustration if a sampling unit according to the present invention, with a selector capillary 2 cm in length 1.3 mm I.C., a sampling capillary 40 cm in length 0.5 mm I.D., is attached to a vacuum aspirator with 100 cms of 1.5 mm I.D. plastic tubing so as to provide an aspiration velocity of 30 cm/sec, the amount of sample collected can be approximately estimated. Over a period of one hour the volumetric flow/hr will be $\pi/4(0.05)^2 \times 30$ cm$^3$/sec$=2.12 \times 10^{-4}$ m$^3$/hr. For coal dust with a Threshold Limit Value (TLV) of 2 mg/m$^3$, containing 20% of respirable particles, $8.48 \times 10^{-5}$ mg of respirable fraction may be collected, which in turn would probably contain approximately 3000 particles assuming a mean diameter of 3$\mu$. While this amount of collected fraction is too small for chemical analysis, the concentration can be readily determined by physical count. In veiw of the cost of analysis, hourly analyses may not be justified but exposure over a long period, say four weeks, may be monitored and determined by physical chemical analysis, since the collected respirable fraction could amount to 0.0135 mg.

We claim:

1. A device for sampling respirable aerosols contained in an atmosphere, comprising:
   a selector capillary tube open at one end thereof to said atmosphere;
   a sampling capillary tube in fluid communication with the other end of said selector tube; and
   aspiration means, connected in series fluid communication with said sampling tube, so as to draw said atmosphere through said selector and sampling tubes at a selected aspiration rate;
   said selector tube having a length and internal diameter selected so as to precipitate therein non-respirable aerosols in said atmosphere at said aspiration rate; and said sampling tube having a length and internal diameter which are longer and smaller respectively so as to selectively precipitate therein substantially all respirable aerosols in said atmosphere at said selected aspiration rate.

2. A sampling device as claimed in claim 1 wherein said aspiration means is an evacuated vessel.

3. A sampling device as claimed in claim 2, including means between said sampling tube and said aspiration means for absorbing a selected gas.

4. A sampling device as claimed in claim 3, wherein said sampling tube and said selector tube are thermoplastic capillary tubes.

5. A sampling device as claimed in claim 3, wherein said sampling tube is a thermoplastic tube wound on spool means.

6. A sampling device as claimed in claim 3, wherein said selected aspiration rate is in the range 10 to 35 cm/sec.

7. A sampling device as claimed in claim 3, wherein the internal diameter of said selector tubing is in the range 0.75 mm to 2.0 mm and the length of said selector tubing is in the range 0.5 to 4 cm.

8. A sampling device as claimed in claim 3, wherein the internal diameter of said sampler tubing is in the range 0.25 to 1.0 mm and the length of said sampler tubing is in the range 20–100 cms.

9. A sampler device as claimed in claim 3, wherein said selector tubing comprises 2 cm of 1.3 mm I.D. tubing and said sampler tubing comprises 40 cm of 0.5 mm I.D. tubing.

* * * * *